United States Patent
Selsted et al.

(10) Patent No.: US 6,444,645 B1
(45) Date of Patent: Sep. 3, 2002

(54) CROSSLINK-STABILIZED INDOLICIDIN ANALOGS

(75) Inventors: Michael E. Selsted, Irvine; Klara Ösapay, Newport Beach, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/099,631

(22) Filed: Jun. 18, 1998

(51) Int. Cl.$^7$ .................. A61K 38/00; A61K 38/04; A61K 39/00; C07K 16/00
(52) U.S. Cl. ............. 514/14; 514/13; 514/14; 514/15; 530/324; 530/327; 530/328; 530/334; 424/450; 424/404; 930/21; 210/764
(58) Field of Search .............. 514/13, 14, 15; 530/324, 327, 328, 334; 424/450, 404; 930/21; 210/764

(56) References Cited

U.S. PATENT DOCUMENTS

| | | |
|---|---|---|
| 5,324,716 A | 6/1994 | Selsted et al. ............ 514/14 |
| 5,547,939 A | 8/1996 | Selsted ................. 514/14 |
| 6,180,604 B1 | 1/2001 | Fraser et al. ............. 514/12 |

FOREIGN PATENT DOCUMENTS

WO    WO 97/08199    3/1997

OTHER PUBLICATIONS

Uchida et al., "Antibacterial activity of the mammalian host defense peptide, indolicidin, and its fragments," abstract *Pept. Chem.*, 124:337665 (1996).
Ahmad et al., "Liposomal entrapment of the neutrophil–derived peptide indolicidin endows it with in vivo antifungal activity", *Biochem. Biophys. Acta*, 1237:109–114 (1995).
Bodanszky, Miklos (ed.), *Principles of Peptide Synthesis,* Springer–Verlag (1993) Table of Contents only.
Del Sal et al., "cDNA Cloning of the Neutrophil Bactericidal Peptide Indolicidin", *Biochem. Biophys. Res. Comm.*, 187(1):467–472 (1992).
Falla and Hancock, "Improved Activity of a Synthetic Indolocidin Analog", *Antimicrob. Agents Chemother.*, 41(4):771–775 (1997).
Gregoriadis, Gregory (ed.), *Liposome Technology: vol. 1—Preparation of Liposomes,* CRC Press, Inc. (1984) Table of Contents only.

Hultmark et al., "Insect immunity. Attacins, a family of antibacterial proteins from *Hyalophora cecropia*", *EMBO J.*, 2(4):571–576 (1993).
Ikehara et al., "Synthesis of a gene for human growth hormone and its expression in *Escherichia coli*", *Proc. Natl. Acad. Sci. USA*, 81:5956–5960 (1984).
Lehrer et al., "Ulstrasensitive assays for endogenous antimicrobial polypeptides", *J. Immuno. Meth.*, 137:167–173 (1991).
Rees et al. (eds.), *Protein Engineering: A Practical Approach,* IRL Press (1992) Table of Contents only.
Setlow, Jane K. (ed.), *Genetic Engineering: Principles and Methods* vol. 15, Plenum Press (1993) Table of Contents Only.
Stachel et al., "Formation of Constrained, Fluorescent Peptides via Trytophan Dimerization and Oxidation", *J. Am. Chem. Soc.*, 118:1225–1226 (1996).
Subbalakshmi et al., "Requirements for antibacterial and hemolytic activities in the bovine neutrophil derived 13–residue peptide indolicidin", *FEBS Letters*, 395:48–52 (1996).
Van Abel et al., "Synthesis and characterization of indolocidin, a tryptophan–rich antimicrobial peptide from bovine neutrophils", *Int'l. J. Peptide Protein Res.*, 45:401–409 (1995).
Wade et al., "All–D amino acid–containing channel–forming antibiotic peptides", *Proc. Natl. Acad. Sci. USA*, 87:4761–4765 (1990).

*Primary Examiner*—Karen Cochrane Carlson
*Assistant Examiner*—Chih-Mim Kam
(74) *Attorney, Agent, or Firm*—Campbell & Flores LLP

(57) ABSTRACT

The present invention relates to crosslink-stabilized analogs of indolicidin, which is a naturally occurring peptide having the amino acid sequence Ile-Leu-Pro-Trp-Lys-Trp-Pro-Trp-Trp-Pro-Trp-Arg-Arg-CONH$_2$ ("Indol 1-13;" SEQ ID NO: 1). The crosslinked indolicidin ("X-indolicidin") analogs of the invention include, for example, analogs such as Indol 1-13(W6,9), which has the structure Ile-Leu-Pro-Trp-Lys-<u>Trp</u>-Pro-Trp-<u>Trp</u>-Pro-Trp-Arg-Arg-CONH$_2$ (SEQ ID NO: 3), and Indol 1-13/6,9C(C6,9), which has the structure Ile-Leu-Pro-Trp-Lys-<u>Cys</u>-Pro-Trp-<u>Cys</u>-Pro-Trp-Arg-Arg-CONH$_2$ (SEQ ID NO: 4), where a crosslink formed between the first and last underlined amino acid residues. In addition, the invention provides nucleic acid molecules encoding the X-indolicidin analogs of the invention, particularly precursors of such analogs. The invention also relates to methods of using an X-indolicidin analog to reduce or inhibit microbial growth or survival by contacting an environment capable of sustaining microbial growth with the X-indolicidin analog.

17 Claims, 9 Drawing Sheets

```
G GAA TTC GAC GAC GAC GAC AAA ATG ATC CTG CCG TGG AAA TGG CCG
c ctt aag ctg ctg ctg ctg ttt tac tag gac ggc acc ttt acc ggc
Eco RI    Asp Asp Asp Asp Lys Met Ile Leu Pro Trp Lys Trp Pro
                              ⇧   ↑

TGG TGG CCG TGG CGT CGT ATG GCT CGT ATC GCT ATG ATC CTG CCG
acc acc ggc acc gca gca tac cga gca tag cga tac tag gac ggc
Trp Trp Pro Trp Arg Arg Met Ala Arg Ile Ala Met Ile Leu Pro
                             ↑                   ↑

TGG AAA TGG CCG TGG TGG CCG TGG CGT CGT ATG GCT CGT ATC GCT
acc ttt acc ggc acc acc ggc acc gca gca tac cga gca tag cga
Trp Lys Trp Pro Trp Trp Pro Trp Arg Arg Met Ala Arg Ile Ala
                                             ↑

ATG ATC CTG CCG TGG AAA TGG CCG TGG TGG CCG TGG CGT CGT ATG
tac tag gac ggc acc ttt acc ggc acc acc ggc acc gca gca tac
Met Ile Leu Pro Trp Lys Trp Pro Trp Trp Pro Trp Arg Arg Met
 ↑                                                        ↑

GCT CGT ATC GCT ATG TAA TAA GTC GAC CGG
cga gca tag cga tac att att cag ctg gcc
Ala Arg Ile Ala Met Stp Stp    Sal I
```

FIGURE 1

CROSSLINK-STABILIZED INDOLICIDIN ANALOGS

This invention was made with government support under grant number AI22931 awarded by the National Institutes of Health. The government has certain rights in the invention.

BACKGROUND OF THE INVENTION

1. Field of the Invention

The present invention relates generally to antimicrobial agents and, more specifically, to crosslink-stabilized indolicidin analogs and methods of using the analogs to reduce-or inhibit microbial growth or survival.

2. Background Information

Infections by microorganisms, including bacteria, viruses and fungi, are a major cause of human morbidity and mortality. Although anyone can be a victim of such infection, the sick and elderly are particularly susceptible. For example, hospitalized patients frequently acquire secondary infections due to a combination of their weakened condition and the prevalence of microorganisms in a hospital setting. Such opportunistic infections result in increased suffering of the patient, increased length of hospitalization and, consequently, increased costs to the patient and the health care system. Similarly, the elderly, particularly those living in nursing homes or retirement communities, are susceptible to infections because of their close living arrangement and the impaired responsiveness of their immune systems.

Numerous drugs are available for treating infections by certain microorganisms. In particular, various bacterial infections have been amenable to treatment by antibiotics. However, the prolonged use of antibiotics since their discovery has resulted in the selection of bacteria that are relatively resistant to these drugs. Furthermore, few if any drugs are effective against microorganisms such as viruses. As a result, continuing efforts are being made to identify new and effective agents for treating infections by a variety of microorganisms.

The identification of naturally occurring compounds that act as antimicrobial agents has provided novel and effective drugs. Many organisms protect themselves by producing natural products that are toxic to other organisms. Frogs, for example, produce a class of peptides, magainins, that are highly toxic if ingested, thus providing a defense mechanism for the frog against potential predators. Magainins have been purified and shown to have antimicrobial activity, thus providing a natural product useful for reducing or inhibiting microbial infections.

Natural products useful as antimicrobial agents also have been purified from mammalian organisms, including humans. For example, the defensins are a class of peptides that have been purified from mammalian neutrophils and demonstrated to have antimicrobial activity. Similarly, indolicidin is a peptide that has been isolated from bovine neutrophils and has antimicrobial activity, including activity against viruses, bacteria, fungi and protozoan parasites. Thus, naturally occurring compounds provide a source of drugs that are potentially useful for treating microbial infections.

Upon identifying naturally occurring peptides useful as antimicrobial agents, efforts began to chemically modify the peptides to obtain analogs having improved properties. Such efforts have resulted, for example, in the identification of indolicidin analogs which, when administered to an individual, have increased selectivity against the infecting microorganisms as compared to the individual's own cells. Thus, the availability of naturally occurring antimicrobial agents has provided new drugs for treating microbial infections and has provided a starting material to identify analogs of the naturally occurring molecule that have desirable characteristics.

Although such natural products and their analogs have provided new agents for treating microbial infections, it is well known that microorganisms can become resistant to drugs. Thus, a need exists to identify agents that effectively reduce or inhibit the growth or survival of microorganisms. The present invention satisfies this need and provides additional advantages.

SUMMARY OF THE INVENTION

The present invention relates to crosslink-stabilized analogs of indolicidin, which is a naturally occurring peptide having the amino acid sequence Ile-Leu-Pro-Trp-Lys-Trp-Pro-Trp-Trp-Pro-Trp-Arg-Arg-$CONH_2$ ("Indol 1-13;" SEQ ID NO: 1). As disclosed herein, crosslink-stabilized indolicidin analogs ("X-indolicidin analogs") of the invention are characterized, in part, by having an intrapeptide crosslink formed, for example, between two Trp residues, to form a di-tryptophan crosslink.

An X-indolicidin analog has the structure: X1-X2-X3-X4-X5-X6-P-X6-X6-P-X6-X7-X7-X8 wherein X1 is Ile, Leu, Val, Ala, Gly or absent; X2 is Ile, Leu, Val, Ala, Gly or absent; X3 is Pro or absent; X4 is Trp, Phe, Cys, Glu, Asp, Lys, $Ala_L$ or absent; X5 is Arg, Lys or absent; X6 is Trp, Phe, Cys, Glu, Asp, Lys or $Ala_L$; X7 is Arg, Lys or absent; and X8 is homoserine, Met, Met-X9-Met or absent, wherein X9 is at least one amino acid; provided that the analog contains at least two amino acid residues that are capable of forming a crosslink; and further provided that if X2 is absent, X1 is absent; if X3 is absent, X1 and X2 are absent; if X4 is absent, X1, X2 and X3 are absent; and if X5 is absent, X1, X2, X3 and X4 are absent. X-indolidicin analogs of the invention are exemplified by the peptide Ile-Leu-Pro-Trp-Lys-<u>Trp</u>-Pro-Trp-<u>Trp</u>-Pro-Trp-Arg-Arg-$CONH_2$ (SEQ ID NO: 3), where the underlining indicates a di-tryptophan crosslink formed between the first and last underlined Trp residues; and by the peptide Ile-Leu-Pro-Trp-Lys-<u>Cys</u>-Pro-Trp-<u>Cys</u>-Pro-Trp-Arg-Arg-$CONH_2$ (SEQ ID NO: 4), where underlining indicates a disulfide crosslink formed between the first and last underlined Cys residues. X-indolicidin analogs have broad spectrum antimicrobial activity.

The invention also provides fusion polypeptides comprising an X-indolicidin analog and a peptide of interest, which can be useful, for example, for facilitating purification of an expressed indolicidin analog. In addition, the invention provides nucleic acid molecules encoding X-indolicidin analogs of the invention, for example, disulfide crosslinked analogs, as well as precursors of such analogs and fusion polypeptides comprising such analogs.

The invention also relates to methods of using an X-indolicidin analog to reduce or inhibit microbial growth or survival in an environment capable of sustaining microbial growth or survival by contacting the environment with the X-indolicidin analog. As such, the invention provides methods of reducing or inhibiting microbial growth or survival on a solid surface, for example, surgical instruments, hospital surfaces, and the like. In addition, methods of the invention are useful for reducing or inhibiting microbial growth or survival in an individual, particularly a mammal such as a human. Thus, the invention provides methods of treating an individual suffering from a pathology caused, at least in part, by microbial infection, by administering an X-indolicidin analog to the individual, thereby reducing the severity of the pathologic condition.

BRIEF DESCRIPTION OF THE DRAWINGS

FIG. 1 shows the nucleotide sequence encoding poly-(Indol(1-13)-Met-Ala-Arg-Ile-Ala-Met)$_3$, (SEQ ID NO: 2) which encodes three copies of Indol 1-13, each separated by Met-Ala-Arg-Ile-Ala-met (SEQ ID NO: 2). The coding (sense) strand is shown in capital letters (SEQ ID NO:11), the antisense strand is shown in lower case letters (SEQ ID NO: 13), and the encoded amino acid sequence (SEQ ID NO:12) is shown using the three letter code ("Stp" indicates STOP codon). The nucleotide and amino acid sequences correspond to SEQ ID NOS: 11 and 12, respectively. Eco RI and Sal I restriction endonuclease sites are indicated. The enterokinase recognition site is singly underlined, with the double arrow indicating the cleavage site. The single arrows denote cyanogen bromide cleavage sites. Dotted underlined tetranucleotide sequences correspond to overlaps in oligonucleotides used for ligation. Double underlined sequences denote primers used for PCR amplification (see Example I.C).

DETAILED DESCRIPTION OF THE INVENTION

Figure 2:
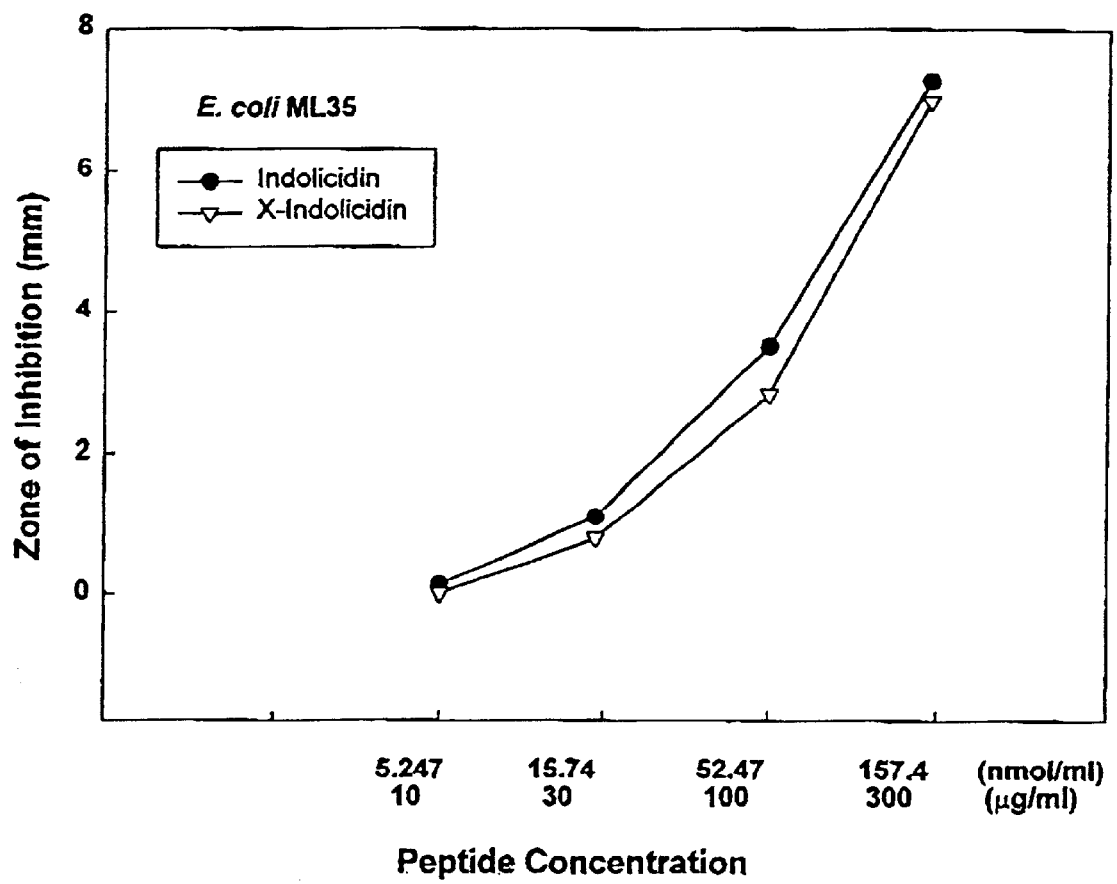
FIG. 2 shows the dose dependent microbistatic activity of indolicidin (Indol 1-13; SEQ ID NO:1)(closed circles) and X-indolicidin (Indol 1-13(W6,9); SEQ ID NO:3)(inverted triangles) on growth of *Escherichia coli* ML35.

The invention provides crosslink-stabilized indolicidin analogs ("X-indolicidin analogs"), which are peptides that are characterized, in part, by having a intrapeptide crosslink. As disclosed herein, an X-indolicidin analog has the general structure: Xaa1-Xaa2-Xaa3-Xaa4-Xaa5-Xaa6-P-Xaa6-Xaa6-P-Xaa6-Xaa7-Xaa7-Xaa8, wherein Xaa1 is Ile, Leu, Val, Ala, Gly or absent; Xaa2 is Ile, Leu, Val, Ala, Gly or absent; Xaa3 is Pro or absent; Xaa4 is Trp, Phe, Cys, Glu, Asp, Lys, Ala$_L$ or absent; Xaa5 is Arg, Lys or absent; Xaa6 is Trp, Phe, Cyst Glu, Asp, Lys or Ala$_L$; Xaa7 is Arg, Lys or absent; and Xaa8 is homoserine, Met, Met-Xaa9-Met or absent, wherein Xaa9 is at least one amino acid. In addition, an X-indolicidin analog contains at least two amino acid residues that are capable of forming a crosslink between their side chains, for example, two Trp residues, which can form a di-tryptophan crosslink; or at least two Cys residues, which. can form a disulfide crosslink; or a lanthionine residue, which can form a monosulfide crosslinkage. A monosulfide crosslink between two Ala$_L$ residues forms a lanthionine residue. Furthermore, if, in an X-indolicidin analog, Xaa2 is absent, Xaa1 is absent; if Xaa3 is absent, Xaa1 and Xaa2 are absent; if Xaa4 is absent, Xaa1, Xaa2 and Xaa3 are absent; and if Xaa5 is absent, Xaa1, Xaa2, Xaa3 and Xaa4 are absent. A crosslink in an X-indolicidin analog can be, for example, between Xaa4, when present, and an Xaa6 residue, or can be between two Xaa6 residues. In addition, an X-indolicidin analog can have more than one crosslink.

As used herein, the term "crosslink" means a covalent bond formed between the reactive groups of two amino acids in a peptide. As such, a crosslink present in an X-indolicidin analog is stable under physiological conditions. A crosslink in an X-indolicidin analog can be formed, for example, between two Trp residues, which form a di-tryptophan crosslink; or between two Cys residues, which form a disulfide bond. In addition, a crosslink can be a monosulfide bond formed by a lanthionine residue. A crosslink also can be formed between other amino acid side chains, for example, a lactam crosslink formed by a transamidation reaction between the side chains of an acidic amino acid and a basic amino acid, such as between the γ-carboxyl group of Glu (or β-carboxyl group of Asp) and the ε-amino group of Lys; or can be a lactone produced, for example, by a crosslink between the hydroxy group of Ser and the γ-carboxyl group of Glu (or β-carboxyl group of Asp); or a covalent bond formed, for example, between two amino acids, one or both of which have a modified side chain.

Indolicidin is a naturally occurring peptide having the amino acid sequence Ile-Leu-Pro-Trp-Lys-Trp-Pro-Trp-Trp-Pro-Trp-Arg-Arg-CONH$_2$ ("Indol 1-13;" SEQ ID NO: 1). Indolicidin (SEQ ID NO: 1) was named based on its tryptophan-rich nature and its microbicidal properties (see U.S. Pat. No. 5,324,716, issued Jun. 28, 1994, which is incorporated herein by reference).

Indolicidin analogs having the general structure H$_2$N-I-L-P-W-K-W-P-W-W-P-W-X (SEQ ID NO: 9), where X designates one or two independently selected amino acids, have been described (see U.S. Pat. No. 5,534,939, issued Aug. 20, 1996). Such indolicidin analogs, like indolicidin (SEQ ID NO: 1), are tryptophan-rich peptides and are characterized, in part, by having improved selectivity as compared to indolicidin (SEQ ID NO: 1). Additional indolicidin analogs also have been described (International Publ. No. WO 97/08199, published Mar. 6, 1997). These previously described indolicidin analogs are distinguishable from those of the present invention in that the previously described analogs do not contain an intrapeptide crosslink.

X-indolidicin analogs of the invention are exemplified by the peptide Ile-Leu-Pro-Trp-Lys-Trp-Pro-Trp-Trp-Pro-Trp-Arg-Arg-CONH$_2$ (SEQ ID NO: 3; "Indol 1-13(W6/9)"), where the underlining indicates a di-tryptophan crosslink formed between the first and last underlined Trp residues (also indicated by "(W6/9)"); and by the peptide Ile-Leu-Pro-Trp-Lys-Cys-Pro-Trp-Cys-Pro-Trp-Arg-Arg-CONH$_2$ (SEQ ID NO: 4; "Indol 1-13/6,9C(C6/9)"), where underlining indicates a disulfide crosslink formed between the first and last underlined Cys residues. As disclosed herein, such X-indolicidin analogs can be relatively more stable to enzymatic degradation than native indolicidin (Example I), and have antimicrobial activity equivalent to indolicidin (Example II).

An X-indolicidin analog of the invention can be based on a full length indolicidin peptide, for example, Indol 1-13 (SEQ ID NO: 1), or on an amino terminal truncated indolicidin analog such as Indol 2-13 (SEQ ID NO: 5) or Indol 3-13 (SEQ ID NO: 6) or a carboxy terminal truncated indolicidin analog such as Indol 1-12 (SEQ ID NO: 7; see Table 1), the non-crosslinked forms of which exhibit antimicrobial activity. An X-indolicidin analog also can be a crosslinked indolicidin analog in which one or more Trp residues is replaced by a Phe residue, since such indolicidin analogs have antimicrobial activity.

comma; thus, Indol 2-13/6,11F indicates an indolicidin analog that lacks one amino terminal amino acid as compared to naturally occurring indolicidin (SEQ ID NO: 1) and contains Phe for Trp substitutions at positions 6 and 11.

The position of a crosslink in an X-indolicidin analog is indicated in parentheses by a designation of the amino acids involved in the crosslink and the positions of the amino acids. For example, Indol 1-13(W6/9) indicates a peptide having the amino acid sequence of naturally occurring indolicidin and containing a di-tryptophan crosslink between the Trp residues at positions 6 and 9 (see Table 1; SEQ ID NO: 3). Indol 1-13/6,9C(C6/9) indicates an indolicidin analog that contains Cys for Trp substitutions at positions 6 and 9 and, further, contains a disulfide crosslink between these Cys residues (see SEQ ID NO: 4; Table 1). For an X-indolicidin analog having a crosslink formed between amino acid residues that do not have a standard one letter code, for example, a monosulfide crosslink formed by a lanthionine residue, the nomenclature can be modified for clarity, such as Indol 1-13/6,9-lanthionine(Lan6,9) or the like.

TABLE 1

INDOLICIDIN AND INDOLICIDIN ANALOGS

| NAME | AMINO ACID SEQUENCE | SEQ ID NO: |
|---|---|---|
| Indol 1-13* | H$_2$N-I-L-P-W-K-W-P-W-W-P-W-R-R-CONH$_2$ | 1 |
| Indol 1-13 (W6/9)** | H$_2$N-I-L-P-W-K-<u>W-P-W-W</u>-P-W-R-R-CONH$_2$ | 3 |
| Indol 1-13/6, 9C (C6/9) | H$_2$N-I-L-P-W-K-<u>C-P-W-C</u>-P-W-R-R-CONH$_2$ | 4 |
| Indol 2-13 | H$_2$N-L-P-W-K-W-P-W-W-P-W-R-R-CONH$_2$ | 5 |
| Indol 3-13 | H$_2$N-P-W-K-W-P-W-W-P-W-R-R-CONH$_2$ | 6 |
| Indol 1-12 | H$_2$N-I-L-P-W-L-W-P-W-W-P-W-R-CONH$_2$ | 7 |
| Indol 2-13/4F | H$_2$N-L-P-F-K-W-P-W-W-P-W-R-R-CONH$_2$ | 8 |
| Indol 2-13/4F (W6/9) | H$_2$N-L-P-F-K-<u>W-P-W-W</u>-P-W-R-R-CONH$_2$ | 10 |

*indolicidin (naturally occurring).
**underlining in sequence indicates crosslink.

For example, an Indol 2-13 (SEQ ID NO: 5) peptide, in which the Trp at position 4 is replaced by Phe (Indol 2-13/4F; SEQ ID NO: 8; see Table 1) can be crosslinked between the Trp residues at positions 6 and 9 to produce Indol 2-13/4F(W6/9) (SEQ ID NO: 10; see Table 1).

Reference to an amino acid position in an X-indolicidin analog is made herein with respect to the amino acid position in naturally occurring indolicidin (SEQ ID NO: 1). As such, the positions are referred to as positions 1 through 13, starting with the Ile residue in SEQ ID NO: 1 (position 1) and ending with the carboxy terminal arginine (position 13). As a result, although Leu is the first amino acid in Indol 2-13 (SEQ ID NO: 5), this Leu residue is referred to as being located at position 2 because this is the location of the corresponding Leu in SEQ ID NO: 1. It follows that SEQ ID NO: 5 is referred to as Indol 2-13 because it begins with an amino acid corresponding to the second amino acid (Leu) of Indol 1-13 (SEQ ID NO: 1; see Table 1).

An X-indolicidin analog or precursor thereof containing a substitution of a residue of naturally occurring indolicidin (SEQ ID NO: 1) with a different amino acid is referred to using the number of the position and the one letter amino acid code. For example, the substitution of the Trp residue at position 4 in indolicidin (Indol 1-13) with a Cys residue results in an indolicidin analog designated Indol 1-13/4C. Similarly, Indol 2-13/6F indicates an indolicidin analog that lacks one amino terminal amino acid as compared to naturally occurring indolicidin (SEQ ID NO: 1) and contains a substitution of Phe for Trp at position 6. Where more than one substitution is made, the positions are separated by a An X-indolicidin analog of the invention is based on the general structure of native, naturally occurring indolicidin (SEQ ID NO: 1), except that various defined amino acid deletions, substitutions or additions are made with respect to indolicidin Xaa1-Xaa2-Xaa3-Xaa4-Xaa5-Xaa6-P-Xaa6-Xaa6-P-Xaa6-Xaa7-Xaa7-Xaa8B. As used herein, the term "amino acid" is used in its broadest sense to mean the naturally occurring amino acids as well as non-naturally occurring amino acids, including amino acid analogs. Thus, reference herein to an amino acid includes, for example, naturally occurring proteogenic (L)-amino acids, as well as (D)-amino acids, chemically modified amino acids such as amino acid analogs, naturally occurring non-proteogenic amino acids such as norleucine, lanthionine or the like, and chemically synthesized compounds having properties known in the art to be characteristic of an amino acid. As used herein, the term "proteogenic" indicates that the amino acid can be incorporated into a protein in a cell through a metabolic pathway.

The amino acid residue at any position in an indolicidin analog having the structure Xaa1-Xaa2-Xaa3-Xaa4-X5-Xaa6-P-Xaa6-Xaa6-P-Xaa6-Xaa7-Xaa7-Xaa8 can be independently selected. As used herein, the term "independently selected" indicates that the choice of an amino acid residue at any one position in an indolicidin analog does not depend on or influence the selection of amino acid residue at any other position in the analog. Thus, the selection of a Trp residue for Xaa6 shown at position 6 of the sequence Xaa1-Xaa2-Xaa3-Xaa4-Xaa5-Xaa6-P-Xaa6-Xaa6-P-Xaa5-Xaa7-Xaa7-Xaa8 does not influence whether, for example, the amino acid present at the Xaa6 shown in position 8 is a Trp residue or a Phe residue, provided that at least two amino acids that form a crosslink, for example, two Trp residues or two Cys residues, are present in the analog.

As disclosed herein, substitution of Cys residues at positions 6 and 9 of Indol 1-13 (SEQ ID NO: 1), and formation of a disulfide crosslink between the two Cys residues, produces Indol 1-13(6,9C)C6/9 (SEQ ID NO: 4, which can have antimicrobial activity equivalent to Indol 1-13 (see Example II). Substitution of various Trp residues in Indol 1-13 (SEQ ID NO: 1) with Phe residues also can result in indolicidin analogs having antimicrobial activity. Thus, the skilled artisan would recognize that various amino acid substitutions can be made in Indol 1-13 (SEQ ID NO: 1) to produce an X-indolicidin analog having antimicrobial activity.

Furthermore, amino terminal truncation of naturally occurring indolicidin results in the production of indolicidin analogs having antimicrobial activity. In addition, indolicidin analogs that lack one carboxy terminal Arg residue, or that contain a Lys substitution for one or both of the carboxy terminal Arg residues, or that lack the carboxy terminal Arg-13 residue and have a Lys substitution for Arg-12 of Indol 1-13 have antimicrobial activity (U.S. Pat. No. 5,547,939, supra, 1996). Accordingly, the skilled artisan will recognize that deletions can be made in Indol 1-13 (SEQ ID NO: 1) to produce truncated X-indolicidin analogs having antimicrobial activity.

Also, in view of the allowability of deletions at the amino terminus or carboxy terminus of Indol 1-13, the skilled artisan will recognize that various amino acid substitutions can be made in the deletable positions without destroying the antimicrobial activity of a derived X-indolicidin analog. Thus, whereas Indol 1-13 (SEQ ID NO: 1) contains an Ile residue at position 1, the skilled artisan, knowing that this Ile can be deleted without destroying antimicrobial activity, would recognize that Ile also can be conservatively substituted with an amino acid such as Leu, Val, Ala or Gly without destroying the antimicrobial activity of an X-indolicidin analog produced therefrom. Similarly, conservative amino acid substitutions are permissible for the Leu at position 2. In addition, the substitution of an Arg residue for Lys at position 5 is permitted, since the presence of a positively charged amino acid at position 5 correlates with antimicrobial activity.

A precursor peptide of an X-indolicidin analog of the invention can be expressed from an encoding nucleic acid molecule in vitro or in vivo in a host cell or can be chemically synthesized. With respect to expressing the analogs, nucleic acid sequences encoding the various indolicidin analogs of the invention can be prepared based, for example, on the disclosure of the indolicidin nucleic acid sequence (Del Sal et al., Biochem. Biophys. Res. Comm. 187:467–472 (1992), which is incorporated herein by reference) and on knowledge in the art of the codons for the amino acids comprising the various disclosed X-indolicidin analogs. Such nucleic acids encoding the X-indolicidin analog precursor can be cloned into an appropriate vector, particularly an expression vector, and the encoded analog can be expressed using an in vitro transcription/translation reaction. In addition, such nucleic acid sequences can be used to construct a synthetic gene encoding a poly-(X-indolicidin analog) polypeptide, which can be cloned into an expression vector and expressed in vivo in a bacterial, insect or mammalian host cells (see Example I.C). It should be recognized that, while reference is made to a nucleic acid encoding an X-indolicidin analog, the nucleic acid encodes a linear precursor peptide that can be crosslinked, for example, in an in vitro reaction, to obtain an X-indolicidin analog. An advantage of expressing a poly-(X-indolicidin analog) polypeptide in vivo is that large amounts can be prepared using, for example, commercial fermentation methods, since the polypeptide form of the analogs does not appear to have substantial antimicrobial activity, then the polypeptide can be cleaved to produce active X-indolicidin analogs or precursors thereof.

An X-indolicidin analog also can be chemically synthesized using well known methods (see, for example, van Abel et al., Internatl. J. Pept. Prot. Res. 45:401–409 (1995), which is incorporated herein by reference; see, also, Example I). An X-indolicidin analog was obtained during acidolytic cleavage and deprotection of Fmoc-assembled Indol 1-13 (SEQ ID NO: 1). During such preparation, a strongly A-320 absorbing material was detected, but is not present in Indol 1-13 prepared from natural sources. Purification and characterization of the A-320 absorbing material revealed that it was 2 atomic mass units lower in mass than naturally occurring Indol 1-13 (SEQ ID NO: 1). The A-320 absorbing material was determined to be Indol 1-13(W6,9) (SEQ ID NO: 3; see Example I.B), which contains a di-tryptophan crosslink between the Trp residues at positions 6 and 9.

When tested for antimicrobial activity, Indol 1-13(W6,9) (SEQ ID NO: 3) demonstrated broad spectrum antimicrobial activity equivalent to native Indol 1-13 (SEQ ID NO: 1; see Example II), but was substantially more stable than native Indol 1-13 (SEQ ID NO: 1) to chymotrypsin digestion (Example I.B). The role of crosslinks in indolicidin analogs was further examined by preparing Indol 1-13/6,9C(C6,9) (SEQ ID NO: 4). The disulfide crosslink in this X-indolicidin analog can stabilize the peptide similarly to Indol 1-13(W6,9) (SEQ ID NO: 3).

An advantage of using chemical synthesis to prepare an X-indolicidin analog is that (D)-amino acids can be substituted for (L)-amino acids, if desired. The incorporation of one or more (D)-amino acids into an X-indolicidin analog can confer, for example, additional stability of the peptide in vitro or, particularly, in vivo, since endogenous proteases generally are ineffective against peptides comprising (D)-amino acids. Naturally occurring antimicrobial peptides that have been chemically synthesized to contain (D)-amino acids maintain their antimicrobial activity (Wade et al., Proc. Natl. Acad. Sci.. USA 87:4761–4765 (1990), which is incorporated herein by reference).

X-indolicidin analogs were synthesized using an automated peptide synthesizer such as an Eppendorf Synostat (Madison Wis.) or a Milligen 9050 (Milford Mass.), although manual methods of solution peptide synthesis also can be used, then crosslinks were formed as desired (Example I.A). Linear precursors of the X-indolicidin analogs were synthesized on a polyethylene glycol-polystyrene (PEG-PS) graft resin using $N^{\alpha}$-Fmoc amino acid derivatives. In addition, a suitable linker such as a peptide amide linker PAL (5-(4-Fmoc-amino methyl-3,5-dimethoxyphenoxy) valeric acid; Fmoc is 9-fluorenyl methyloxycarbonyl; Milligen) or XAL (5-(9-Fmoc-amino xanthen-2-oxy)valeric acid) was used to produce carboxamide end groups. However, the skilled artisan would know that other resins, amino acid derivatives and methods of modifying amino acid reactive groups or the amino terminus, for example, by acetylation, or the carboxy terminus can be used to obtain a desired indolicidin analog (see, for example, Protein Engineering: A practical approach (IRL Press 1992); Bodanszky, Principles of Peptide Synthesis (Springer-Verlag 1984), each of which is incorporated herein by reference). The synthesized X-indolicidin analogs were purified by reversed phase HPLC and characterized by mass spectroscopy, absorption spectroscopy, acid-urea gel electrophoresis and analytical HPLC (see Example I) or can be purified and characterized using other routine methods of peptide purification and analysis.

Selective modification of a reactive group, other than the production of crosslinks, can impart desirable characteristics to an indolicidin analog. The choice of including such a modification is determined, in part, by the characteristics required of the peptide. Such modifications can result, for example, in X-indolicidin analogs having greater antimicrobial selectivity or potency than naturally occurring indolicidin. As used herein, the term "antimicrobial selectivity" refers to the relative amount of antimicrobial activity of an X-indolicidin analog against a microorganism as compared to its activity against the environment to which it is administered, particularly its activity against normal cells in a treated individual. For example, an X-indolicidin analog that is characterized by having antimicrobial activity that is equivalent to native indolicidin, but having decreased hemolytic activity as compared to native indolicidin, is considered to have greater antimicrobial selectivity than native indolicidin.

Indolicidin analogs having greater antimicrobial selectivity than naturally occurring indolicidin have been described. For example, indolicidin analogs truncated at the carboxy terminus or having one or more lysine substitutions for the carboxy terminal arginines in naturally occurring indolicidin have antimicrobial activity similar to indolicidin, but have decreased hemolytic activity (U.S. Pat. No. 5,547,939, supra, 1996). Also, indolicidin analogs in which all of the Trp residues were substituted with Phe, but not analogs having Ala for Pro substitutions, had greater antimicrobial selectivity than native indolicidin (Subbalakshmi et al., *FEBS Lett.* 395:48–52 (1996), which is incorporated herein by reference). Indolicidin analogs containing various other amino acid substitutions or modifications, for example, carboxymethylation of the carboxy terminus also have desirable properties (Fall and Hancock, *Antimicr. Agents Chemother.* 41:771–775 (1997), which is incorporated herein by reference; see, also, WO 97/08199, supra, 1997). None of the previously described indolicidin analogs, however, contain an intrachain crosslink. The antimicrobial selectivity of an X-indolicidin analog can be determined using the methods disclosed herein (see Example II) or using routine methods such as those described in the above cited references.

As disclosed herein, an X-indolicidin analog, Indol 1-13 (W6,9) (SEQ ID NO: 3), demonstrated broad spectrum antimicrobial activity similar to that of native indolicidin (Indol 1-13; SEQ ID NO: 1; Example II). As used herein, the term "broad spectrum," when used in reference to the antimicrobial activity of an X-indolicidin analog, refers to the ability of the analog to reduce or inhibit the survival or proliferative ability of various prokaryotic and eukaryotic microorganisms. For example, indolicidin analogs of the invention can exhibit antimicrobial activity against protozoans such as Giardia lamblia, Chlamydia sp. and Acanthamoeba sp.; viruses, particularly enveloped viruses such as HIV-1; yeast and fungi such as Cryptococcus and Candida; various genera of gram negative and gram positive bacteria, including Escherichia, Salmonella and Staphylococcus; and helminths such as liver flukes. Antimicrobial activity can occur through microbicidal inhibition, which refers to the ability of an X-indolicidin analog to reduce or inhibit the survival of a microorganism by killing or irreversibly damaging it, or through microbistatic inhibition, which refers to the ability of an X-indolicidin analog to reduce or inhibit the growth or proliferative ability of a target microorganism without necessarily killing it.

Indolicidin analogs containing a carboxy terminal homoserine residue ("Indol-Hse" analogs) maintain antimicrobial activity. The determination that an Indol-Hse analog maintains antimicrobial activity is significant because an Hse group remains at the carboxy terminus of a peptide following cyanogen bromide cleavage of the peptide at a Met residue. Since native indolicidin does not contain an internal Met residue and since indolicidin analogs lacking internal Met residues can be produced, such analogs are not cleaved upon exposure to cyanogen bromide. The Hse at the carboxy terminus of a peptide typically exists as an equilibrium state between the lactone and carboxylate forms. An Indol-Hse analog can be amidated at the carboxy terminus.

The disclosed ability of an Indol-Hse analog to maintain antimicrobial activity provides a means to produce substantial quantities of X-indolicidin analog precursors by expressing a poly-(Indol-Met)$_N$ polypeptide, where "N" is the number of times the Indol-Met sequence is repeated, and cleaving the polypeptide with cyanogen bromide to produce "IN" Indol-Hse analog peptides (see Example I.C). Crosslinks then can be formed in the precursor peptides to produce X-indolicidin analogs.

A method of producing polypeptide X-indolicidin precursors can be performed in vivo in a host cell because poly-(Indol-Met)$_N$ polypeptides do not exhibit substantial antimicrobial activity. Such a method is performed, for example, by synthesizing a nucleic acid sequence encoding the Indol portion of the analog and a carboxy terminal Met; ligating the nucleic acid sequences, such that the encoded peptides are maintained in the same reading frame, to produce a synthetic gene comprising a concatemer having "N" repeats of the Indol-Met coding sequence; cloning the synthetic gene into an expression vector such that the encoded poly-(Indol-Met)$_N$ is expressed from the promoter in the vector; transforming a host cell with the vector; expressing the encoded poly-(Indol-Met)$_N$ polypeptide; and cleaving the polypeptide with cyanogen bromide to produce "N" Indol-Hse analogs. Crosslinks then can be formed in the peptides to produce X-indolicidin analogs. Thus, the invention provides X-indolicidin analogs containing a carboxy terminal homoserine residue.

Purification of an expressed poly-(Indol-Met)$_N$ polypeptide is facilitated by further linking the synthetic gene to a nucleic acid sequence encoding a peptide that is capable of being bound by a molecule. Such a peptide can be a ligand or a receptor, which can be specifically bound by an appropriate receptor or ligand, respectively; or a peptide that is specifically bound by an antibody. In addition, a peptide linked to a poly-(Indol-Met)$_N$ polypeptide can be any peptide of interest, for example, a peptide such as alkaline phosphatase or green fluorescent protein, which provide a means to detect the presence of the fusion polypeptide.

For facilitating purification of a poly-indolicidin analog polypeptide, the linked peptide can be, for example, maltose binding protein, which binds maltose or a maltose containing oligosaccharide such as amylose; glutathione-S-transferase (GST), which binds glutathione; His-6, which is bound by a metal ion such as nickel ion or cobalt ion; the FLAG epitope, which is bound by anti-FLAG antibody; or any other peptide for which a specific antibody or other ligand or receptor is available. If desired, the molecule, for example, glutathione, that binds the peptide (GST), can be attached to a solid support such as a chromatography matrix and an expressed poly-(Indol-Met)$_N$-GST fusion polypeptide can be purified from contaminating host cell proteins by passage over the matrix. If desired, the fusion polypeptide can be eluted from the matrix and treated with cyanogen bromide; or the fusion polypeptide, while attached to the matrix, can be exposed to cyanogen bromide, thereby releasing only the Indol-Hse analog precursors of the corresponding X-indolicidin analog. Thus, the invention provides fusion polypeptides comprising an X-indolicidin analog precursor linked to a peptide of interest. As used herein, the term "precursor," when used in reference to X-indolicidin, means a linear peptide than can form an intrapeptide crosslink to produce an X-indolicidin analog.

The invention also provides nucleic acid molecules encoding the X-indolicidin analogs of the invention, specifically linear peptide or polypeptide precursors of the X-indolicidin analogs. The skilled artisan will know that the nucleotide sequences of the nucleic acid molecules of the invention can be determined based on the amino acid sequence of an X-indolicidin analog and knowledge of the codons encoding the various amino acids. Such codons can be selected using computer assisted methods. One or another degenerate codon, for example, one of the six codons encoding Arg or one of the six codons encoding Leu or the like, can be selected as desired, for example, to prevent (or include) the insertion of a restriction endonuclease site in the X-indolicidin analog coding sequence. The nucleic acid molecules of the invention are useful, for example, to produce X-indolicidin analog precursors in vitro using an appropriate transcription/translation system or in vivo using an appropriate expression system, after which intrachain crosslinks can be formed in the precursors to produce X-indolicidin analogs. The nucleic acid molecules of the invention can be polydeoxyribonucleotide sequences (DNA) or polyribonucleotide sequences (RNA), as desired, and can contain linkers, adapters or the like to facilitate cloning or concatemerization in the appropriate frame.

An X-indolicidin analog having antimicrobial activity can be applied to an environment capable of sustaining the survival or growth of a microorganism or to an environment at risk of supporting such survival or growth, thus providing a means for reducing or inhibiting microbial growth or survival. Accordingly, the invention relates to methods of using an X-indolicidin analog to reduce or inhibit microbial growth by contacting an environment capable of sustaining microbial growth or survival with the X-indolicidin analog.

As used herein, reference to "an environment capable of sustaining survival or growth of a microorganism" means a gaseous, liquid or solid material, including a living organism, in or upon which a microorganism can live or propagate. In view of the broad range of environments that allow the survival or growth of microorganisms as diverse, for example, as viruses, bacteria and fungi, and further in view of the disclosed effectiveness of X-indolicidin analogs against a broad spectrum of such microorganisms, the range of such environments that can be treated using a method of the invention necessarily is broad and includes, for example, a tissue or bodily fluid of an organism such as a human; a liquid such as water or an aqueous solution, for example, contact lens solution; a food such as a food crop, a food product or a food extract; an object such as the surface of an instrument used, for example, to prepare food or to perform surgery; and a gas such as that used for anesthetization in preparation for surgery.

A method of the invention encompasses administering to the environment an effective amount of an X-indolicidin analog such that the analog can contact a microorganism in the environment, thereby reducing or inhibiting the ability of the microorganism to grow or survive. An X-indolicidin analog can be used in a variety of procedures for reducing or inhibiting the survival or growth of microorganisms, including the microbicidal inhibition of survival of a microorganism as well as the microbistatic inhibition of growth. As such, an X-indolicidin analog can be used, for example, as a therapeutic agent, a food preservative, a disinfectant or a medicament.

An X-indolicidin analog can be used as a therapeutic agent for treating a patient suffering from a bacterial, viral, fungal or other infection due to a microorganism susceptible to the antimicrobial activity of the analog. Thus, the invention provides methods of treating an individual suffering from a pathology caused, at least in part, by microbial infection, by administering an X-indolicidin analog to the individual under conditions that allow the analog to contact the infecting microorganisms, thereby reducing or inhibiting the survival or growth of the microorganism and alleviating the severity of the infection.

For use as a therapeutic agent, the X-indolicidin analog can be formulated with a pharmaceutically acceptable carrier to produce a pharmaceutical composition, which can be administered to the individual, which can be a human or other mammal. A pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester.

A pharmaceutically acceptable carrier can contain physiologically acceptable compounds that act, for example, to stabilize or increase the absorption of the X-indolicidin analog. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; or other stabilizers or excipients. One skilled in the art would know that the choice of a pharmaceutically acceptable carrier, including a physiologically acceptable compound, depends, for example, on the route of administration of the composition.

A pharmaceutical composition containing an X-indolicidin analog can be administered to an individual by various routes, including by intravenous, subcutaneous, intramuscular, intrathecal or intraperitoneal injection; orally, as an aerosol spray; or by intubation. If desired, the X-indolicidin analog can be incorporated into a liposome, a non-liposome lipid complex, or other polymer matrix, which further can have incorporated therein, for example, a second drug useful for treating the individual. Use of an indolicidin incorporated into liposomes, for example, has been demonstrated to have antifungal activity in vivo (Ahmad et al., *Biochim. Biophys. Acta* 1237:109–114 (1995), which is incorporated herein by reference). Liposomes, which consist of phospholipids or other lipids, are nontoxic, physiologically acceptable and metabolizable carriers that are relatively simple to make and administer (Gregoriadis, *Liposome Technology*, Vol. 1 (CRC Press, Boca Raton Fla., 1984), which is incorporated herein by reference). The skilled artisan will select a particular route and method of administration based, for example, on the location of a microorganism in a subject, the particular characteristics of the microorganism, and the specific X-indolicidin analog that is administered.

Food and food products also can be treated with X-indolicidin analogs for the purpose of preserving the food or eliminating or preventing infection by microorganisms. For example, shellfish and poultry products routinely harbor enteric pathogenic microorganisms. The growth or survival of such microorganisms can be reduced or inhibited by contacting the product with an X-indolicidin analog. Food crops such as fruits, vegetables and grains can be treated with an X-indolicidin analog in order to reduce or inhibit post-harvest spoilage caused by microorganisms, for example, by administering the analog topically using an aerosolized form of the analog. In addition, transgenic plants or animals useful in the food industry can be produced by introducing a nucleic acid molecule encoding a precursor of an X-indolicidin analog of the invention into the germline cells of such organisms, particularly a precursor of an X-indolicidin analog that contains disulfide crosslinks, since disulfide crosslinks can form spontaneously in cells in vivo. Methods for producing transgenic plants and animals are well known and routine in the art.

An X-indolicidin analog also can be used as a disinfectant to reduce or inhibit the survival or growth of microorganisms on an object or in a solution. An X-indolicidin analog can be used to treat essentially any object or solution that can sustain microbial growth, where the survival or growth of the microorganisms is undesirable. In particular, an object or solution that comes into contact with a mammal such as a human, for example, baby wipes, diapers, band-aids, towelettes, make-up products and eyewash and contact lens solutions can be treated with an X-indolicidin analog. In such methods, the X-indolicidin analog can be applied topically to the object or can be added to the solution or can be in an aerosolized form in a gas.

In order to exhibit antimicrobial activity in an environment, an effective amount of an X-indolicidin analog is administered to the environment. As used herein, the term "effective amount" refers to the amount of an X-indolicidin analog that reduces or inhibits the survival or growth of a microorganism in an environment. In particular, an effective amount of an X-indolicidin analog produces only minimal effects against the environment, although the level of an acceptable deleterious effect is weighed against the benefit caused by the antimicrobial effect.

An X-indolicidin analog can be administered to a subject such as a human systemically at a dose ranging from 1 to 100 mg/kg body weight, for example, at a dose of about 10 to 80 mg/kg, particularly about 10 to 50 mg/kg, and the X-indolicidin analog can be incorporated in liposomes, if desired. In addition, an X-indolicidin analog can be administered topically to an environment, which can be a human subject, or can be placed in a solution, at a concentration of about 0.1 to 10 mg/ml, for example, at a concentration of about 0.5 to 5 mg/ml. Although X-indolicidin analogs generally are effective in microgram amounts, an effective amount for administration to a particular environment will depend, in part, on the environment. For example, when administered to a mammal such as a human, an X-indolicidin analog, in addition to having antimicrobial activity, can have hemolytic activity as a side effect. The skilled artisan will recognize that the level of such side effects must be considered in prescribing a treatment and must be monitored during the treatment period, and will adjust the amount of the analog that is administered accordingly. An effective amount also will vary depending, for example, on the characteristics of the target microorganism, the extent of prior infection or growth and the specific X-indolicidin analog administered. In addition, an effective amount depends on the form in which the X-indolicidin analog is administered. For example, incorporation of native indolicidin into liposomes allowed administration of a higher amount than "free" indolicidin, without producing unacceptable side effects, such that fungal infection in mice could be cured (Ahmad et al., supra, 1995).

The following examples are intended to illustrate but not limit the present invention.

EXAMPLE I

Preparation and Characterization of X-Indolicidin Analogs

This example provides methods for preparing and characterizing X-indolicidin analogs.

A. Chemical synthesis of Indol 1-13

Indol(1-13) was assembled on an Fmoc-PAL-PEG-PS resin at 0.2 mmol scale on a Millipore 9050 Plus continuous-flow peptide synthesizer. The resin was swollen for 30 min in DMF before starting the synthesis. Fmoc-chemistry was utilized throughout.

Fmoc-cleavage was performed with 2%. DBU-2% piperidine/DMF solution for 1 to 5 min. The following protecting groups were used: Arg(Pbf), Lys(tBoc), Trp (tBoc), Glu(OtBu), Ser(tBu), Cys(Trt). All amino acids were coupled by BOP/HOBt/NMM activation, using 5 min preactivation, 60 min coupling time, and 3-fold molar excess amino acid in each coupling reaction. Coupling of Ile, Leu, Trp(6) and Trp(9) were repeated (double coupled) for 40 min. After the last coupling, the Fmoc-group was cleaved from the peptide and the peptidyl-resin was washed with DCM and ethanol, then dried for 24 hr in vacuo.

For cleavage and deprotection, the peptidyl-resin was swollen in DCM in a manual reaction vessel, excess DCM was removed by filtration, and the resin was cooled to 0° C. Protecting groups were removed and the peptide was cleaved from the resin with reagent K (TFA-phenol-water-thioanisole-1,2-ethanedithiol; 82.5:5:5:5:2.5) using a ratio of 1.5 ml reagent K/gram peptidyl-resin. The reaction vessel was shaken for 4 hr, then the resin was filtered, washed with fresh reagent K (1 ml/g resin), followed by DCM (3×10 ml/g resin) and, finally, 50% acetic acid /water (3×10 ml/g resin). The combined filtrates were placed in a separatory funnel and the aqueous phase was extracted twice more with DCM. The aqueous peptide solution was diluted with distilled water to a 10% final acetic acid concentration then freeze-dried. The lyophilization was repeated with the 5% acetic acid/water solution of the peptide. The crude product was isolated as a white fluffy powder.

The crude synthetic peptide was dissolved in 5% acetic acid/water (0.5 mg/ml peptide concentration) and subjected to RP-HPLC purification (van Abel et al., supra, 1995). A Vydac preparative C-18 reversed-phase column (25×100 mm) was used for purification and a Vydac C-18 analytical column (0.46×25 mm) for purity assessment. In both cases, gradients of acetonitrile (with 0.1% TFA) and water (0.1% TFA) were used for chromatographic fractionation. Elution of peptide elution was monitored at 220 nm and 280 nm. The appropriate HPLC fractions were combined, concentrated by centrifugal evaporation, and lyophilized.

B. Characterization of Indol 1-13(W6,9)

During the acidolytic cleavage and deprotection of Fmoc-assembled Indol 1-13 (SEQ ID NO: 1), a strongly A-320 absorbing material was detected in the synthetic product that is absent from indolicidin prepared from natural sources. The A-320 absorbing material was purified by cation exchange HPLC, using a sulfoethyl cation exchange column (0.45×20 cm). The column was loaded with 1.5 mg of sample dissolved in 100 mM NaOAc containing 25% acetonitrile and eluted in the same solvent isocratically. The A-320 absorbing material was collected and purified by RP-HPLC using the conditions described above and, as discussed below, determined to be the X-indolicidin, Indol 1-13(W6,9).

The purified A-320 absorbing material was characterized by electrospray mass spectroscopy. The A-320 material was 2 atomic mass units lower in mass than naturally occurring Indol 1-13 (SEQ ID NO: 1). The monoisotopic mass of indolicidin was 1905.88 (theoretical 1906.05) as compared to 1904.13 (theoretical 1904.05) for the A-320 absorbing material. UV spectroscopy revealed, in addition to absorbance at A-320, which is absent for native indolicidin, absorbance at A-218 and A-280; native indolicidin also shows absorbance at A-218 and A-280. The A-320 material also was highly fluorescent (emission at 400 nm) as determined by spectrofluorimetry with an excitation of 325 nm.

Edman sequence analysis of the A-320 material revealed a dramatic drop in the yield of Trp-6 and Trp-9. In conjunction with the very high fluorescence emission, these results indicate the presence of an extended ring system. Further analysis for Trp-Trp connectivity was carried out by digesting the A-320 absorbing material with trypsin and chymotrypsin and characterizing the resulting fragments by mass spectrometry. The masses of the products confirmed that Trp-6 and Trp-9 were crosslinked through the 5 carbon of the respective indol rings, generating a di-tryptophan crosslink. Accordingly, the A-320 material was designated Indol 1-13(W6,9) (SEQ ID NO: 3).

Indol 1-13 (SEQ ID NO: 1) and Indol 1-13(W6,9) (SEQ ID NO: 3) were subjected to enzymatic degradation for 6, 24, 48 and 96 hr with α-chymotrypsin (1% by weight) in 0.1 M Tris buffer (pH 7.7) at 37° C., then analyzed by RP-HPLC. All of the native indolicidin (SEQ ID NO: 1) was digested within 6 hr of incubation. Approximately 85% of the Indol 1-13(W6,9) (SEQ ID NO: 3) was digested after 3 hr, but the remaining undigested material was stable for at least the 18 hr incubation period. These results indicate that an X-indolicidin analog, which contains an intrachain crosslink, is stabilized with respect to proteolytic degradation as compared to linear native indolicidin.

Di-tryptophan crosslinks were formed in an indolicidin or indolicidin analog peptide using a modification of the method of Stachel et al. *J. Amer. Chem. Soc.* 118:1225 (1996), which is incorporated herein by reference). Approximately 1 mg of purified peptide was dissolved in about 100 µl trifluoroacetic acid and incubated under nitrogen at room temperature for 0.5 to 18 hr. The sample was dried in vacuo, washed with 100 µl chloroform and redried in vacuo. The dried peptide was dissolved in about 1.0 ml of 1,4-dioxane containing 0.6 µmol dichloro,dicyano-quinone and stirred for 0.1 to 2 hr at room temperature. The products of the optimized incubation were purified by RP-HPLC, monitoring elution at 320 nm.

Indol 1-13/6,9C (see SEQ ID NO: 4), which contains Cys for Trp substitutions at positions 6 and 9, was prepared using the method described above. The side chain protecting groups were removed by acidolysis and the disulfide bond was formed by allowing air oxidation at pH 7–9 to produce Indol 1-13/6,9C(C6,9) (SEQ ID NO: 4). Air oxidation of reduced Indol/6,9C is carried out at a peptide concentration of 100 µg/ml in 0.1 M ammonium bicarbonate (pH 8) or in 0.1 M Tris-HCl (pH 8) or other aqueous solvent at pH 8. The solution is stirred at room temperature, in room air, for 2 to 72 hr, with intermittent testing of the solution using Ellman's reagent, to determine when no free sulfhydryl groups remain. The oxidized peptide is purified by RP-HPLC and the disulfide formation is confirmed by electrospray or MALDI-TOF mass spectrometry.

C. Expression of Indol-Hse analogs:

Indol-Hse was expressed from a recombinant construct encoding three repeats of the mature peptide, each separated by a hexapeptide spacer sequence; poly-(Indol(1-13)-Met-Ala-Arg-Ile-Ala-Met)$_3$ (SEQ ID NO: 2). The recombinant indolicidin was produced as a fusion polypeptide with a maltose-binding protein (MBP) and recovered by cleavage with cyanogen bromide.

The multicopy indolicidin encoding DNA sequence was assembled from six synthetic oligonucleotides. The oligonucleotides were phosphorylated and assembled by annealing and ligation each fragment (Ikehara et al., *Proc. Natl. Acad. Sci. USA* 81:2956–5960 (1984), which is incorporated herein by reference). The oligonucleotides (2.5 nmol each) were phosphorylated by treatment with 10 mmol ATP at pH 8.0, heated for 2 min in boiling water, then 9.5 units of polynucleotide kinase was added and the samples were incubated at 37° C. for 120 min. The reaction was stopped by incubating the samples for 15 min at 70° C. Phosphorylated fragments and nonphosphorylated ends were mixed, heated for 2 min in boiling water, and the annealing of the pairs was completed after slow cooling to 15° C. and incubation over night. The samples were phenol/chloroform purified and EtOH precipitated. The annealed DNA mixtures were mixed together and treated with T4 ligase 1.2 units for 15 hr at 15° C. The mixture was heated for 2 min at 70° C. to inactivate the ligase.

A 211 base pair (bp) ligation product was isolated from an agarose gel following electrophoresis using the WIZARD PCR purification kit (Promega; Madison Wis.); PCR was performed using the primers as shown in FIG. 1 (double underlined sequence). The purified 211 bp PCR product was digested with Sal I and Eco RI, then ligated into the Sal I and Eco RI sites of precut pMAL-c2 vector (New England BioLabs; Beverly MA). Transformation of INVαF' *E. coli* was carried out with the TA cloning kit as per the manufacturers directions (Invitrogen; La Jolla Calif.). The DNA sequence shown in FIG. 1 was confirmed by dideoxy sequencing.

The INVαF' cells containing the poly-indolicidin analog pMAL-c2 fusion polypeptide were grown overnight in 15 ml LB media containing 100 µg/ml ampicillin at 37° C. with constant shaking. Ten ml of the overnight culture was transferred into 1 liter of fresh LB/ampicillin media containing 0.2% glucose and incubated with constant shaking for 4 hr to an $OD_{620}$=0.500. IPTG was added to a final concentration of 0.3 mM and the culture was incubated for an additional 4 hr, then the cells were harvested by centrifugation at 4° C.

The cell pellet was suspended in 20 ml ice cold lysis buffer (0.01 M Tris-HCl, pH 8.0; 1 mM each of PMSF, DTT and EDTA; 2 mg/ml lysozyme), then mixed slowly for 30 min on ice. 1.6 ml of 10% sodium deoxycholate and 63 µl of a 2 mg/ml solution of DNAse I were added and the mixture was incubated for an additional 30 min on ice. 3.2 ml of 2% protamine sulfate was added and the mixture was mixed for 20 min on ice. Soluble fusion polypeptide was obtained in the supernatant after centrifugation for 30 min 12,000 rpm. The fusion polypeptide was purified using an amylose affinity resin (New England BioLabs).

The lysis supernatant was diluted 10 to 25-fold with column buffer (0.2 M NaCl; 0.02 M Tris-HCl pH 8.0; 1 mM each DTT and EDTA) before applying to the column. From 2 liters of bacterial culture, approximately 80 mg of maltose binding protein (MBP)-indolicidin fusion polypeptide was purified by amylose affinity chromatography. The purified fusion polypeptide (80 mg) was dialyzed against 1% acetic acid, lyophilized, and dissolved in 4 ml of 80% formic acid containing 160 mg CNBr. The solution was purged with nitrogen, and incubated at room temperature for 5 hr. The solution was diluted 10 fold with water, lyophilized, then the digest was purified by RP-HPLC. The recovery of Indol(1-13)-Hse was approximately 50% of the theoretical yield.

Alternatively, an MBP-indolicidin fusion polypeptide can be prepared having the sequence Met-Ala-Arg-Ile-Ala-Met (SEQ ID NO: 2) in place of the first Met residue in the poly-indolicidin and after an enterokinase cleavage site. Such an MBP-indolicidin fusion polypeptide can be cleaved first with enterokinase, to release the MBP portion of the fusion polypeptide. The poly-indolicidin portion then can be treated with CNBr, to release the Indol-Hse analogs, which can be purified as above.

The results discussed above indicate that poly-indolicidin analog polypeptides can be produced in vivo in a bacterial expression system, without killing the host microorganism, and, therefore, provides a means to produce substantial amounts of Indol-Hse analogs and, therefore, X-indolicidin analogs by effecting crosslinks as described above.

EXAMPLE II

Antimicrobial Activity of X-Indolicidin Analogs

This example demonstrates that Indol 1-13(W6,9) (SEQ ID NO: 3) exhibits broad spectrum antimicrobial activity similar to the activity of native indolicidin (SEQ ID NO 1).

Antimicrobial activity was characterized using a microbial inhibition method, including a modified plate diffusion assay (Hultmark et al., *EMBO J.* 2:571–573 (1983); Lehrer et al., *J. Immunol. Meth.* 137:167–173 (1991), each of which is incorporated herein by reference). Nutrient-containing agar (or agarose) plates were seeded with *E. coli* ML35, *C. neoformans* 271A, *S. aureus* 207A or *C. albicans* 16820. Five to ten $\mu$l Indol 1-13 (SEQ ID NO: 1) or Indol 1-13 (W6,9) in 10 mM PIPES, pH 7.4 (final concentration of 10, 30, 100 or 300 $\mu$g/ml) were placed into small wells formed in the solid agarose plates. Following an initial incubation interval of 1 to 4 hr, the well-containing layer was overlayed with enriched (2×normal) solid medium in order to support microbial growth outside the perimeter of inhibition. After overnight incubation at 30° C. to 37° C., the antimicrobial activity was quantitated by measuring the clear zones around each well (zone of inhibition).

Figure 3:
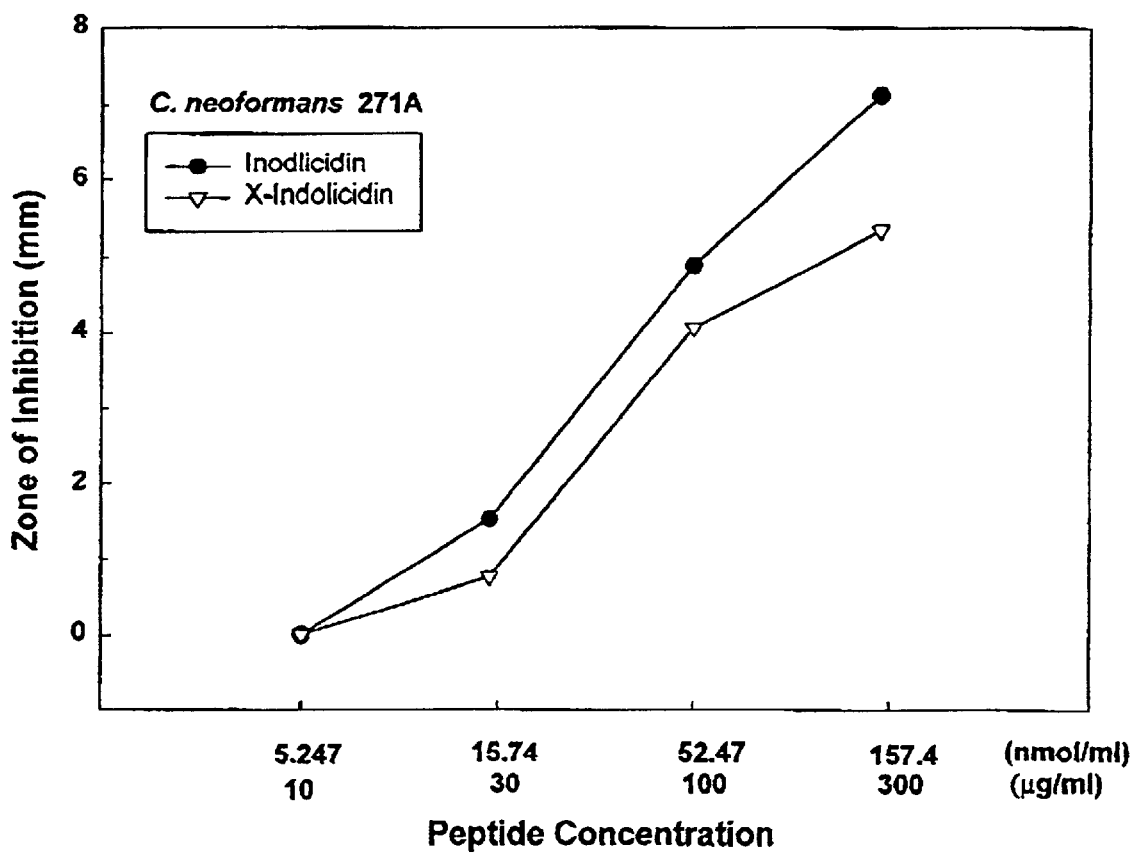
FIG. 3 shows the dose dependent microbistatic activity of indolicidin (Indol 1-13; SEQ ID NO:1)(closed circles) and X-indolicidin (Indol 1-13(W6,9); SEQ ID NO:3)(inverted triangles) on growth of *Cryptococcus neoformans* 271A.
Figure 4:
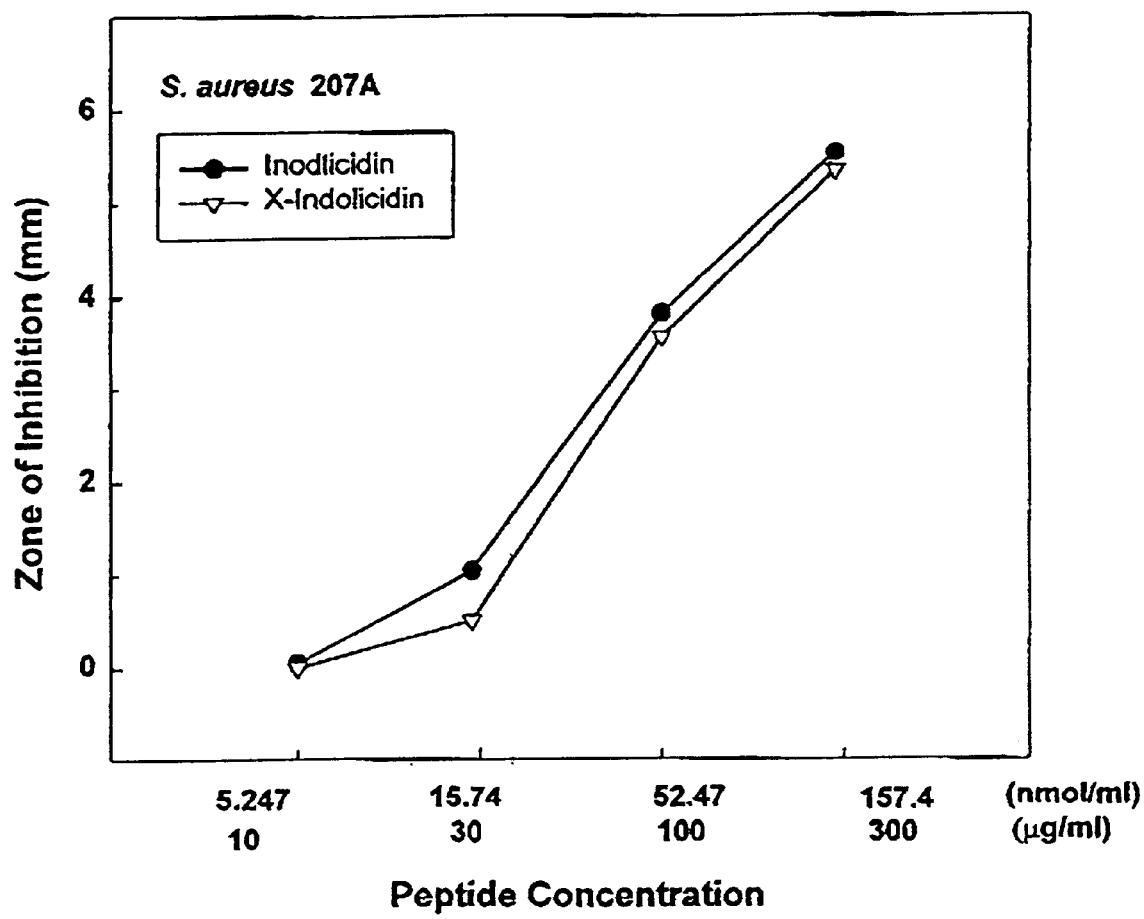
FIG. 4 shows the dose dependent microbistatic activity of indolicidin (Indol 1-13; SEQ ID NO:1)(closed circles) and X-indolicidin (Indol 1-13(W6,9); SEQ ID NO:3)(inverted triangles) on growth of *Staphylococcus aureus* 207A.
Figure 5:
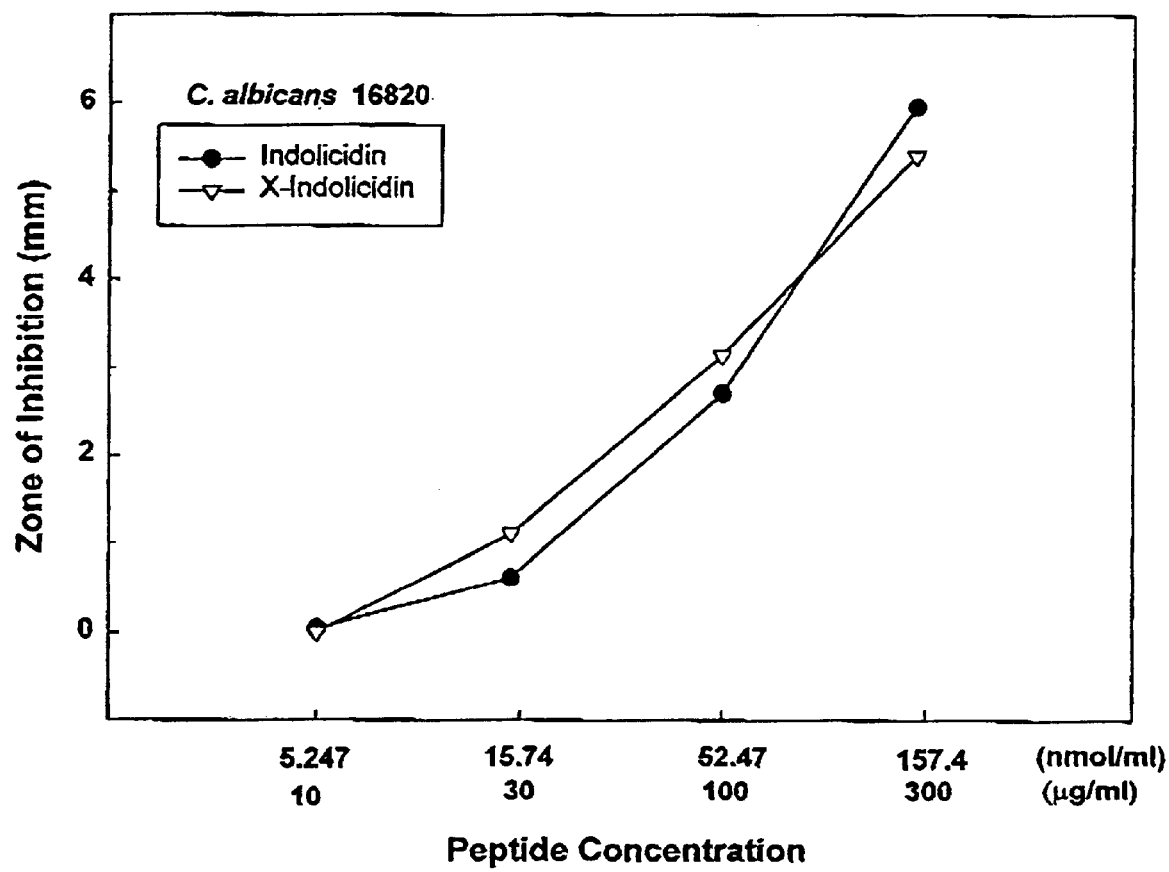
FIG. 5 shows the dose dependent microbistatic activity of indolicidin (Indol 1-13; SEQ ID NO:1)(closed circles) and X-indolicidin (Indol 1-13(W6,9); SEQ ID NO:3) (inverted triangles) on growth of *Candida albicans* 16820.

Indol 1-13 (SEQ ID NO: 1) and Indol 1-13(W6,9) (SEQ ID NO: 3) inhibited the growth of each microorganism tested in a dose dependent manner and the zones of inhibition for each peptide were approximately the same for a given microorganism (see FIGS. 2 through 5). These results indicate that an X-indolicidin analog has essentially the same microbistatic activity as native indolicidin.

Microbicidal activity of Indol 1-13 (SEQ ID NO: 1) and Indol 1-13(W6,9) (SEQ ID NO: 3) for the same four microorganisms (see above) also was examined. Microbicidal activity was measured by first incubating the target organism with the peptide in 10 mM PIPES buffer (pH 7.4), then plating the suspension to quantitate surviving microorganisms.

Cultures were grown to mid log phase in an appropriate medium, harvested, washed, and resuspended to 1–2×10$^7$ colony forming units (CFU) per ml. To conserve peptide, the incubation volume usually was 0.05 ml, with the final cell concentration being 1–2×10$^6$ CFU/ml. Peptide stock solutions, usually made up in 0.0% acetic acid, were diluted in the incubation buffer to a final concentration of 1 $\mu$g/ml to 30 $\mu$g/ml, and the incubation was initiated by addition of an appropriate volume of the bacterial or fungal stock suspension to the prewarmed (37° C.) peptide-buffer mixture. *E. coli* and *S. aureus* were incubated with peptide for 30 min; *C. albicans* was incubated for 60 min; and *C. neoformans* was incubated for 4 hr. Following incubation, 50 $\mu$l or 100 $\mu$l samples were removed and diluted serially, then plated on nutrient-containing agar plates. Killing activity was quantitated by determining the reduction in CFU relative to appropriate control incubations.

Figure 6:
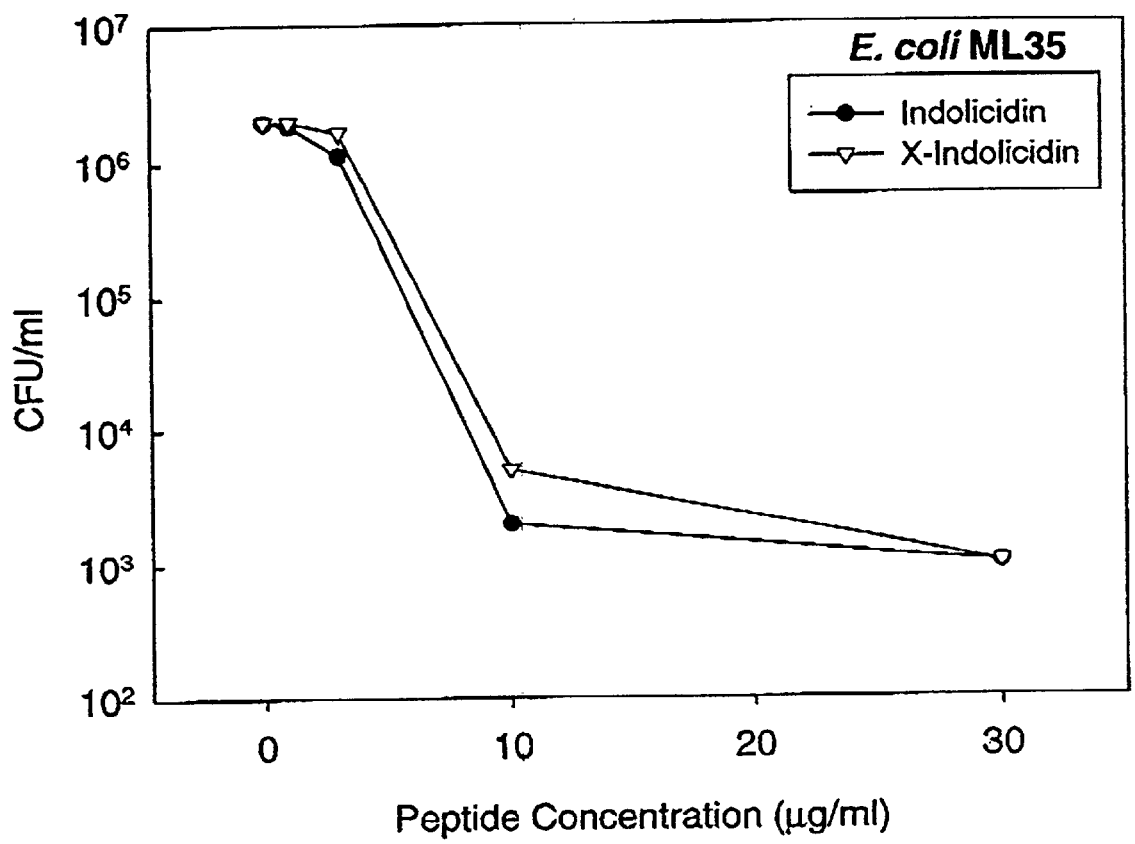
FIG. 6 shows the dose dependent microbicidal activity of indolicidin (Indol 1-13; SEQ ID NO:1)(closed circles) and X-indolicidin (Indol 1-13(W6,9); SEQ ID NO:3)(inverted triangles) on growth of *E. coli* ML35.
Figure 7:
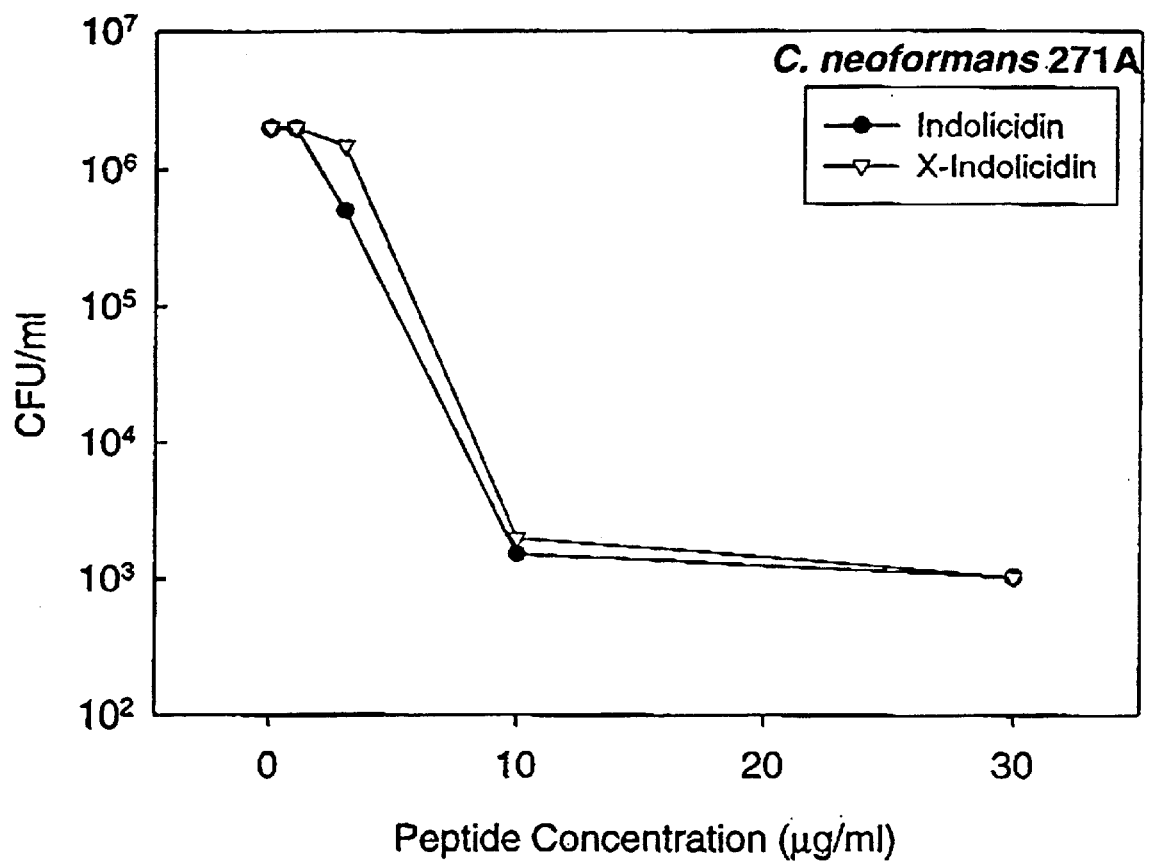
FIG. 7 shows the dose dependent microbicidal activity of indolicidin (Indol 1-13; SEQ ID NO:1)(closed circles) and X-indolicidin (Indol 1-13(W6,9); SEQ ID NO:3)(inverted triangles) on growth of *C. neoformans* 271A.
Figure 8:
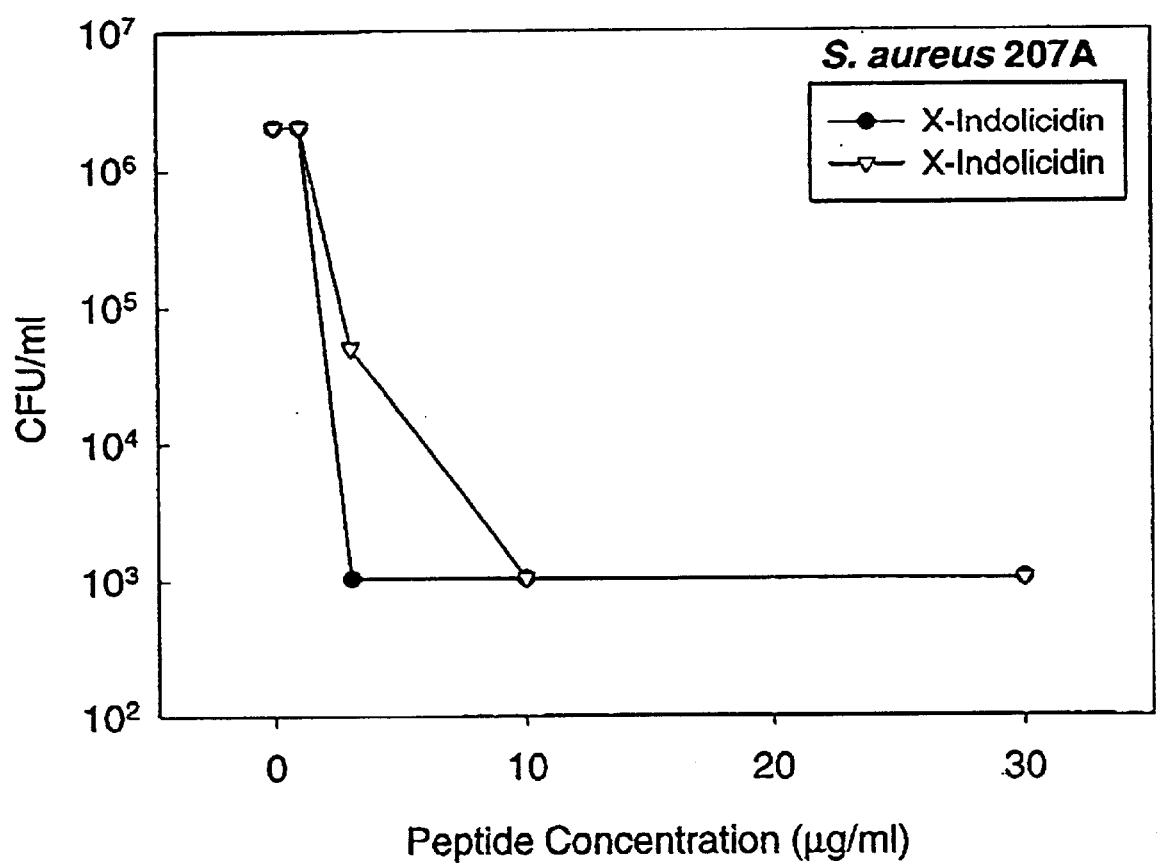
FIG. 8 shows the dose dependent microbicidal activity of indolicidin (Indol 1-13; SEQ ID NO:1)(closed circles) and X-indolicidin (Indol 1-13(W6,9); SEQ ID NO:3)(inverted triangles) on growth of *S. aureus* 207A.
Figure 9:
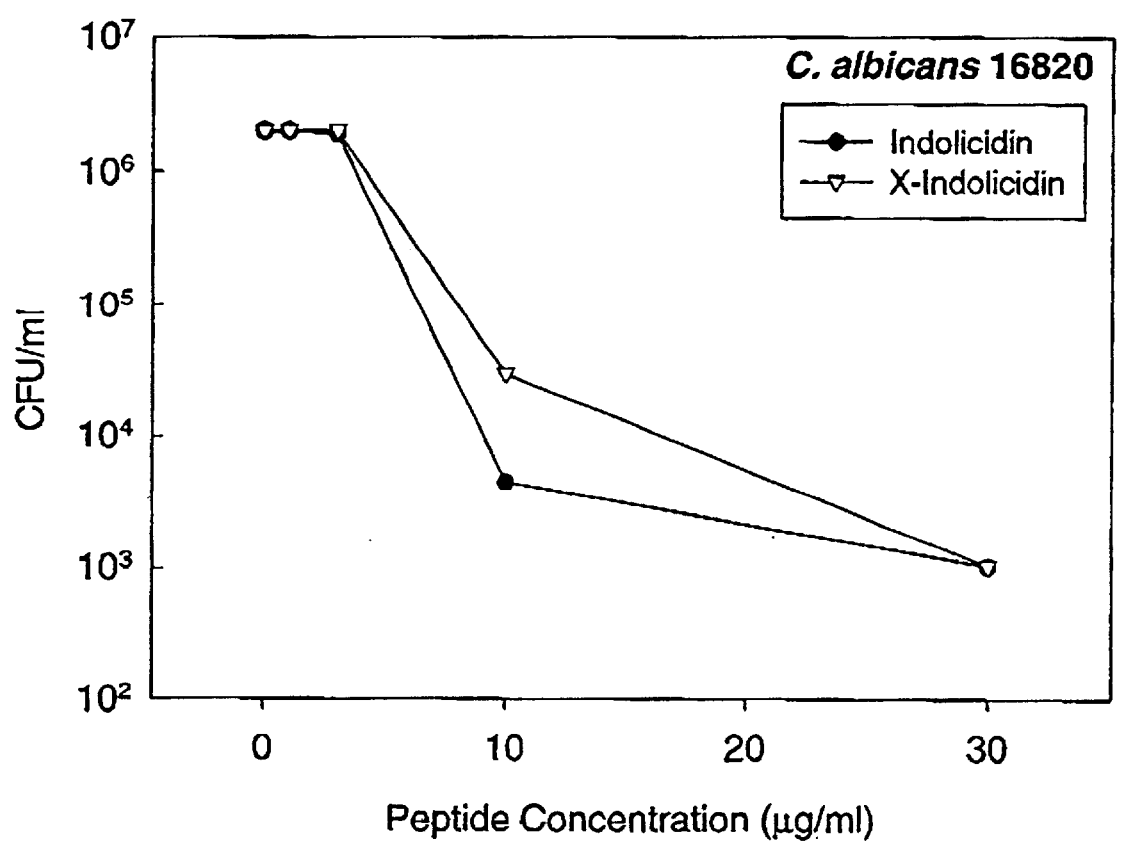
FIG. 9 shows the dose dependent microbicidal activity of indolicidin (Indol 1-13; SEQ ID NO:1)(closed circles) and X-indolicidin (Indol 1-13(W6,9); SEQ ID NO:3) (inverted triangles) on growth of *C. albicans* ML35.

Indol 1-13 (SEQ ID NO: 1) and Indol 1-13(W6,9) (SEQ ID NO: 3) had very similar microbicidal activity (see FIGS. 6 through 9). At 10 $\mu$g/ml, both peptides reduced survival of *E. coli*, *S. aureus* and *C. neoformans* by greater than three orders of magnitude, with minimal additional killing observed at 30 $\mu$g/ml peptide. Both peptides also reduced survival of *C. albicans* by about two orders of magnitude at 10 $\mu$g/ml, and by greater than three orders of magnitude at 30 $\mu$g/ml. These results demonstrate that an X-indolicidin analog has microbicidal activity against a variety of different microorganisms and, with the results of the microbistatic assays discussed above, demonstrate that an X-indolicidin analog, like indolicidin, has broad spectrum antimicrobial activity.

Although the invention has been described with reference to the examples provided above, it should be understood that various modifications can be made without departing from the spirit of the invention. Accordingly, the invention is limited only by the claims.

What is claimed is:

1. A crosslinked indolicidin (X-indolicidin) analog having the amino acid sequence:

Xaa1-Xaa2-Xaa3-Xaa4-Xaa5-Xaa6-Pro-Xaa6-Xaa6-Pro-Xaa5-Xaa7-Xaa7-Xaa5, wherein: Xaa1 is Ile, Leu, Val, Ala, Gly or absent;
Xaa2 is Ile, Leu, Val, Ala, Gly or absent;
Xaa3 is Pro or absent;
Xaa4 is Trp, Phe, Cys, Glu, Asp, Lys, Ala$_L$ or absent;
Xaa5 is Arg, Lys or absent;
Xaa6 is Trp, Phe, Cys, Glu, Asp, Lys, or Ala$_L$;
Xaa7 is Arg, Lys or absent; and
Xaa8 is homoserine (Hse), Met, Met-Xaa9-Met or absent;
wherein Xaa9 is one or more amino acids; provided that a crosslink can be formed between two amino acids selected from the group consisting of:

a) Xaa4, when present, and an Xaa6; and
b) a first Xaa6 and another Xaa6; and further provided that:
if Xaa2 is absent, Xaa1 is absent;
if Xaa3 is absent, Xaa1 and Xaa2 are absent;
if Xaa4 is absent, Xaa1, Xaa2 and Xaa3 are absent; and
if Xaa5 is absent, Xaa1, Xaa2, Xaa3 and Xaa4 are absent,
and wherein said crosslinked indolicidin analog has antimicrobial activity.

2. The X-indolicidin analog of claim 1, further comprising a C-terminal amide.

3. The X-indolicidin analog of claim 1, which has the amino acid sequence:

$H_2N$-Ile-Leu-Pro-Trp-Lys-Trp-Pro-Trp-Trp-Pro-Trp-Arg-Arg-$CONH_2$ (SEQ ID NO: 3), wherein the cross link is formed between the Trp amino acids at positions 6 and 9.

4. The X-indolicidin analog of claim 1, which has the amino acid sequence:

$H_2N$ -Ile-Leu-Pro-Trp-Lys-Cys-Pro-Trp-Cys-Pro-Trp-Arg-Arg-$CONH_2$ (SEQ ID NO: 4), and wherein the cross link is formed between the Cys amino acids at positions 6 and 9.

5. The X-indolicidin analog of claim 1, wherein said crosslink is a di-tryptophan crosslink.

6. The X-indolicidin analog of claim 1, wherein said crosslink is a disulfide crosslink.

7. The X-indolicidin analog of claim 1, wherein said crosslink is selected from the group consisting of a monosulfide crosslink, a lactam and a lactone.

8. A fusion polypeptide, comprising the X-indolicidin analog of claim 1 linked to a peptide, wherein said peptide is capable of being specifically bound by a molecule, and wherein said peptide and said molecule, respectively, are selected from the group consisting of: glutathione-S-transferase and glutathione; maltose binding protein and maltose; and His-6 and a metal ion.

9. The indolicidin analog of claim 1, which has antimicrobial activity against a microorganism selected from the group consisting of a gram positive bacteria, a gram negative bacteria, a yeast and a fungus.

10. The indolicidin analog of claim 9, wherein said microorganism is selected from the group consisting of *Staphylococcus aureus, Escherichia coli, Candida albicans, Salmonella typhimurium* and *Cryptococcus neoformans*.

11. The indolicidin analog of claim 1, which has antimicrobial activity against a protozoan.

12. The indolicidin analog of claim 11, wherein said protozoan is selected from the group consisting of Giardia sp. and Acanthamoeba sp.

13. The indolicidin analog of claim 1, which has antimicrobial activity against a virus.

14. The indolicidin analog of claim 13, wherein said virus is human immunodeficiency virus-1.

15. A pharmaceutical composition, comprising the X-indolicidin analog of claim 1 and a pharmaceutically acceptable carrier.

16. The pharmaceutical composition of claim 15, which is associated with a liposome.

17. The pharmaceutical composition of claim 15, which is associated with a non-liposome lipid complex.

* * * * *

UNITED STATES PATENT AND TRADEMARK OFFICE
CERTIFICATE OF CORRECTION

PATENT NO.      : 6,444,645 B1
DATED           : September 3, 2002
INVENTOR(S)     : Selsted et al.

It is certified that error appears in the above-identified patent and that said Letters Patent is hereby corrected as shown below:

Column 3,
Line 11, please delete "met" and replace with -- Met --.

Column 23,
Line 64, please delete "Xaa5-Xaa7-Xaa7-Xaa5" and replace with
-- Xaa6-Xaa7-Xaa7-Xaa8 --.

Signed and Sealed this

Sixteenth Day of September, 2003

JAMES E. ROGAN
*Director of the United States Patent and Trademark Office*

SEQUENCE LISTING

```
<160> NUMBER OF SEQ ID NOS:  13

<210> SEQ ID NO 1
<211> LENGTH: 13
<212> TYPE: PRT
<213> ORGANISM: Bos taurus
<220> FEATURE:
<221> NAME/KEY: MOD_RES
<222> LOCATION: (13)
<223> OTHER INFORMATION: AMIDATION

<400> SEQUENCE: 1
```

```
Ile Leu Pro Trp Lys Trp Pro Trp Trp Pro Trp Arg Arg
 1               5                   10
```

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 2

```
Met Ala Arg Ile Ala Met
 1               5
```

<210> SEQ ID NO 3
<211> LENGTH: 13
<212> TYPE: PRT
<213> ORGANISM: Artificial Sequence
<220> FEATURE:
<221> NAME/KEY: MOD_RES
<222> LOCATION: (13)
<223> OTHER INFORMATION: AMIDATION
<223> OTHER INFORMATION: Description of Artificial Sequence: Synthetic
      Construct

<400> SEQUENCE: 3

```
Ile Leu Pro Trp Lys Trp Pro Trp Trp Pro Trp Arg Arg
 1               5                   10
```

<210> SEQ ID NO 4
<211> LENGTH: 13
<212> TYPE: PRT
<213> ORGANISM: Artificial Sequence
<220> FEATURE:
<221> NAME/KEY: MOD_RES
<222> LOCATION: (13)
<223> OTHER INFORMATION: AMIDATION
<223> OTHER INFORMATION: Description of Artificial Sequence: Synthetic
      Construct

<400> SEQUENCE: 4

```
Ile Leu Pro Trp Lys Cys Pro Trp Cys Pro Trp Arg Arg
 1               5                   10
```

<210> SEQ ID NO 5
<211> LENGTH: 12
<212> TYPE: PRT
<213> ORGANISM: Artificial Sequence
<220> FEATURE:
<221> NAME/KEY: MOD_RES
<222> LOCATION: (12)
<223> OTHER INFORMATION: AMIDATION
<223> OTHER INFORMATION: Description of Artificial Sequence: Synthetic
      Construct

<400> SEQUENCE: 5

```
Leu Pro Trp Lys Trp Pro Trp Trp Pro Trp Arg Arg
 1               5                   10
```

<210> SEQ ID NO 6
<211> LENGTH: 11
<212> TYPE: PRT
<213> ORGANISM: Artificial Sequence
<220> FEATURE:
<221> NAME/KEY: MOD_RES
<222> LOCATION: (11)
<223> OTHER INFORMATION: AMIDATION
<223> OTHER INFORMATION: Description of Artificial Sequence: Synthetic
      Construct

```
<400> SEQUENCE: 6

Pro Trp Lys Trp Pro Trp Trp Pro Trp Arg Arg
 1               5                  10

<210> SEQ ID NO 7
<211> LENGTH: 12
<212> TYPE: PRT
<213> ORGANISM: Artificial Sequence
<220> FEATURE:
<221> NAME/KEY: MOD_RES
<222> LOCATION: (12)
<223> OTHER INFORMATION: AMIDATION
<223> OTHER INFORMATION: Description of Artificial Sequence: Synthetic
      Construct

<400> SEQUENCE: 7

Ile Leu Pro Trp Leu Trp Pro Trp Trp Pro Trp Arg
 1               5                  10

<210> SEQ ID NO 8
<211> LENGTH: 12
<212> TYPE: PRT
<213> ORGANISM: Artificial Sequence
<220> FEATURE:
<221> NAME/KEY: MOD_RES
<222> LOCATION: (12)
<223> OTHER INFORMATION: AMIDATION
<223> OTHER INFORMATION: Description of Artificial Sequence: Synthetic
      Construct

<400> SEQUENCE: 8

Leu Pro Phe Lys Trp Pro Trp Trp Pro Trp Arg Arg
 1               5                  10

<210> SEQ ID NO 9
<211> LENGTH: 12
<212> TYPE: PRT
<213> ORGANISM: Artificial Sequence
<220> FEATURE:
<221> NAME/KEY: SITE
<222> LOCATION: (12)
<223> OTHER INFORMATION: Xaa is an  independently selected amino acid
<223> OTHER INFORMATION: Description of Artificial Sequence: Synthetic
      Construct

<400> SEQUENCE: 9

Ile Leu Pro Trp Lys Trp Pro Trp Trp Pro Trp Xaa
 1               5                  10

<210> SEQ ID NO 10
<211> LENGTH: 12
<212> TYPE: PRT
<213> ORGANISM: Artificial Sequence
<220> FEATURE:
<221> NAME/KEY: MOD_RES
<222> LOCATION: (12)
<223> OTHER INFORMATION: AMIDATION
<223> OTHER INFORMATION: Description of Artificial Sequence: Synthetic
      Construct

<400> SEQUENCE: 10

Leu Pro Phe Lys Trp Pro Trp Trp Pro Trp Arg Arg
 1               5                  10

<210> SEQ ID NO 11
<211> LENGTH: 211
<212> TYPE: DNA
<213> ORGANISM: Artificial Sequence
```

```
<220> FEATURE:
<221> NAME/KEY: CDS
<222> LOCATION: (8)..(196)
<223> OTHER INFORMATION: Description of Artificial Sequence: Synthetic
      Construct

<400> SEQUENCE: 11 ggaattc gac gac gac gac aaa atg atc ctg ccg tgg aaa tgg ccg tgg            49
        Asp Asp Asp Asp Lys Met Ile Leu Pro Trp Lys Trp Pro Trp
        1               5                   10 tgg ccg tgg cgt cgt atg gct cgt atc gct atg atc ctg ccg tgg aaa            97
Trp Pro Trp Arg Arg Met Ala Arg Ile Ala Met Ile Leu Pro Trp Lys
15                  20                  25                  30 tgg ccg tgg tgg ccg tgg cgt cgt atg gct cgt atc gct atg atc ctg           145
Trp Pro Trp Trp Pro Trp Arg Arg Met Ala Arg Ile Ala Met Ile Leu
                35                  40                  45 ccg tgg aaa tgg ccg tgg tgg ccg tgg cgt cgt atg gct cgt atc gct           193
Pro Trp Lys Trp Pro Trp Trp Pro Trp Arg Arg Met Ala Arg Ile Ala
            50                  55                  60 atg taataagtcg accgg                                                      211
Met <210> SEQ ID NO 12
<211> LENGTH: 63
<212> TYPE: PRT
<213> ORGANISM: Artificial Sequence
<220> FEATURE:
<223> OTHER INFORMATION: Description of Artificial Sequence: Synthetic

<400> SEQUENCE: 12

Asp Asp Asp Asp Lys Met Ile Leu Pro Trp Lys Trp Pro Trp Trp Pro
1               5                   10                  15

Trp Arg Arg Met Ala Arg Ile Ala Met Ile Leu Pro Trp Lys Trp Pro
                20                  25                  30

Trp Trp Pro Trp Arg Arg Met Ala Arg Ile Ala Met Ile Leu Pro Trp
            35                  40                  45

Lys Trp Pro Trp Trp Pro Trp Arg Arg Met Ala Arg Ile Ala Met
        50                  55                  60

<210> SEQ ID NO 13
<211> LENGTH: 211
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 13
ccttaagctg ctgctgctgt tttactagga cggcaccttt accggcacca ccggcaccgc          60
agcataccga gcatagcgat actaggacgg cacctttacc ggcaccaccg gcaccgcagc         120
ataccgagca tagcgatact aggacggcac ctttaccggc accaccggca ccgcagcata         180
ccgagactag cgatacatta ttcagctggc                                          211
```